United States Patent
Venugopal et al.

(10) Patent No.: US 11,980,492 B2
(45) Date of Patent: May 14, 2024

(54) SYSTEM AND METHOD FOR DEEP-LEARNING BASED ESTIMATION OF CORONARY ARTERY PRESSURE DROP

(71) Applicant: GE PRECISION HEALTHCARE LLC, Wauwatosa, WI (US)

(72) Inventors: Prem Venugopal, Clifton Park, NY (US); Cynthia Elizabeth Landberg Davis, Niskayuna, NY (US); Jed Douglas Pack, Glenville, NY (US); Jhimli Mitra, Niskayuna, NY (US); Soumya Ghose, Niskayuna, NY (US); Peter Michael Edic, Marcy, NY (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 287 days.

(21) Appl. No.: 17/520,204

(22) Filed: Nov. 5, 2021

(65) Prior Publication Data
US 2023/0142152 A1 May 11, 2023

(51) Int. Cl.
*A61B 6/00* (2006.01)
*A61B 6/03* (2006.01)
(Continued)

(52) U.S. Cl.
CPC .............. *A61B 6/504* (2013.01); *A61B 6/032* (2013.01); *A61B 6/037* (2013.01); *A61B 6/507* (2013.01);
(Continued)

(58) Field of Classification Search
CPC ......... A61B 6/032; A61B 6/035; A61B 6/037; A61B 6/4429; A61B 6/4435; A61B 6/4441; A61B 6/4447; A61B 6/481; A61B 6/486; A61B 6/487; A61B 6/503; A61B 6/504; A61B 6/507; A61B 6/52; A61B 6/5205;
(Continued)

(56) References Cited

U.S. PATENT DOCUMENTS

| | | | |
|---|---|---|---|
| 8,315,812 B2 * | 11/2012 | Taylor | G16B 45/00 382/128 |
| 8,526,699 B2 | 9/2013 | Mittal et al. | |

(Continued)

OTHER PUBLICATIONS

Sharma, Puneet, et al.; "A Framework for Personalization of Coronary Flow Computations During Rest and Hyperemia", 34th Annual International Conference of IEEE EMBS, 2012; pp. 6665-6668.
(Continued)

*Primary Examiner* — Allen C. Ho
(74) *Attorney, Agent, or Firm* — Fletcher Yoder P.C.

(57) ABSTRACT

A computer-implemented method includes generating, via a processor, synthetic vessels. The method also includes performing, via the processor, three-dimensional (3D) computational fluid dynamics (CFD) on the synthetic vessels for different flow rates to generate 3D CFD data. The method further includes extracting, via the processor, 3D image patches from the synthetic vessels. The method even further includes obtaining, via the processor, pressure drops across the 3D image patches from the 3D CFD data. The method yet further includes training, via the processor, a deep neural network utilizing the 3D image patches, the pressure drops, and associated flow rates to generate a trained deep neural network.

20 Claims, 7 Drawing Sheets

(51) Int. Cl.
*A61B 6/50* (2024.01)
*G06N 3/08* (2023.01)
*G06T 7/11* (2017.01)

(52) U.S. Cl.
CPC .......... *A61B 6/5217* (2013.01); *A61B 6/5241* (2013.01); *G06N 3/08* (2013.01); *G06T 7/11* (2017.01)

(58) Field of Classification Search
CPC ... A61B 6/5211; A61B 6/5217; A61B 6/5223; A61B 6/5229; A61B 6/5235; A61B 6/5241; A61B 6/482; A61B 6/484
USPC ......................................... 378/8, 42, 62, 901
See application file for complete search history.

(56) References Cited

U.S. PATENT DOCUMENTS

| | | | | |
|---|---|---|---|---|
| 8,630,468 | B2* | 1/2014 | Klingenbeck | A61B 6/507 382/128 |
| 9,259,287 | B2* | 2/2016 | Mansi | A61B 34/10 |
| 9,265,473 | B2* | 2/2016 | Mittal | A61B 6/507 |
| 9,320,487 | B2* | 4/2016 | Mittal | A61B 5/02007 |
| 9,349,178 | B1 | 5/2016 | Itu et al. | |
| 9,700,219 | B2 | 7/2017 | Sharma et al. | |
| 9,761,004 | B2 | 9/2017 | Mittal et al. | |
| 9,846,765 | B2* | 12/2017 | Audigier | G16H 50/50 |
| 9,974,453 | B2 | 5/2018 | Fonte et al. | |
| 10,010,255 | B2 | 7/2018 | Fonte et al. | |
| 10,157,490 | B2* | 12/2018 | Redel | A61B 90/36 |
| 10,231,784 | B2* | 3/2019 | Hettrick | A61B 6/032 |
| 10,420,478 | B2* | 9/2019 | Redel | A61B 6/487 |
| 10,575,810 | B2 | 3/2020 | Sankaran et al. | |
| 10,580,526 | B2* | 3/2020 | Ma | G16H 50/50 |
| 10,699,407 | B2* | 6/2020 | Isgum | A61B 6/5217 |
| 10,748,438 | B2* | 8/2020 | Audigier | G09B 23/303 |
| 10,762,637 | B2* | 9/2020 | Gulsun | G06N 3/045 |
| 10,867,383 | B2* | 12/2020 | Redel | A61B 6/504 |
| 10,937,549 | B2* | 3/2021 | Ma | A61B 5/0261 |
| 10,964,017 | B2* | 3/2021 | Pack | G06N 3/084 |
| 11,386,563 | B2* | 7/2022 | Figueroa-Alvarez | G06T 7/215 |
| 11,406,318 | B2* | 8/2022 | Tearney | A61B 5/0066 |
| 11,523,744 | B2* | 12/2022 | Freiman | G16H 50/30 |
| 11,744,472 | B2* | 9/2023 | Zhao | A61B 5/021 600/481 |

OTHER PUBLICATIONS

Taylor, Charles A., et al.; "Computational Fluid Dynamics Applied to Cardiac Computed Tomography for Noninvasive Quantification of Fractional Flow Reserve", Journal of American College of Cardiology, vol. 61, No. 22, 2013; pp. 2233-2241.

Van der Horst, Arjen, et al.; "Towards Patient-Specific Modeling of Coronary Hemodynamics in Healthy and Diseased State", Computational and Mathematical Methods of Medicine, vol. 2013, Article ID 393792, accepted 2013; pp. 1-15.

Shahzad, Rahil, et al.; "Automatic segmentation, detection and quantification of coronary artery stenoses on CTA", Int J Cardiovasc Imaging (2013) 29; pp. 1847-1859.

Itu, Lucian, et al.; "A machine-learning approach for computation of fractional flow reserve from coronary computed tomography", J Appl Physiol 121: 2016; pp. 42-52.

* cited by examiner

SYSTEM AND METHOD FOR DEEP-LEARNING BASED ESTIMATION OF CORONARY ARTERY PRESSURE DROP

BACKGROUND

The subject matter disclosed herein relates to systems and methods for deep-learning-based estimation of coronary artery pressure drop.

Volumetric medical imaging technologies use a variety of techniques to gather three-dimensional information about the body. For example, a computed tomography (CT) imaging system measures the attenuation of X-ray beams passed through a patient from numerous angles. Based upon these measurements, a computer is able to reconstruct cross-sectional images of the portions of a patient's body responsible for the radiation attenuation. As will be appreciated by those skilled in the art, these images are based upon separate examination of a series of angularly-displaced measurements. It should be pointed out that a CT system produces data that represent the distribution of linear attenuation coefficients of the scanned object. The data are then reconstructed to produce an image that is typically displayed on a screen, and may be printed or reproduced on film.

For example, in the field of CT angiography (CTA), vasculature and other circulatory system structures may be imaged, typically by administration of a radio-opaque dye prior to imaging. Visualization of the CTA data typically is performed in a two-dimensional manner, i.e., slice-by-slice, or in a three-dimensional manner, i.e., volume visualization, which allows the data to be analyzed for vascular pathologies. For example, the data may be analyzed for aneurysms, vascular calcification, renal donor assessment, stent placement, vascular blockage, and vascular evaluation for sizing and/or runoff. Once a pathology is located, quantitative assessments of the pathology may be made of the on the original two-dimensional slices.

Atherosclerosis is a vascular disease in which cholesterol and other material accumulate along the inner lining of an artery forming atheromas or plaques. These plaque deposits, can over time, lead to a local narrowing of the blood vessel, often referred to as a stenosis. In the presence of a substantial stenosis, blood flow to the tissues downstream becomes severely restricted. Initially, severity of a stenosis was based purely on geometry, such as the percent reduction in lumen diameter. However, it was soon realized that anatomic significance of a stenosis did not always translate to functional significance. The concept of fractional flow reserve (FFR) was introduced to address this issue. It is defined as the ratio of pressure distal to the stenosis to the pressure proximal to it and measures the hemodynamic resistance of the stenosis relative to the resistance of the coronary microcirculation. Typically, FFR is measured at the time of invasive coronary angiography by inserting a tiny guide wire through a standard diagnostic catheter. A sensor at the tip of the wire measures pressure. Low values of FFR indicate a hemodynamically significant stenosis and clinical trials have demonstrated that intervention can be deferred when FFR>0.8.

It is estimated that approximately 60 percent of invasive angiographies performed are diagnostic in nature and therefore unnecessary. Thus, the estimation of coronary FFR by combining computational fluid dynamics (CFD) modeling with CTA images has emerged as a non-invasive method for identifying ischemia-causing lesions. An accurate estimation of the FFR distribution along the coronary tree can be obtained with a three-dimensional (3D) CFD model of the large coronary epicardial arteries. However, the computation times can be large with this approach. Efforts to reduce computation times have involved utilizing a one-dimensional (1D) model. However, some of these 1D models involve several approximations and therefore FFR predictions may not be as accurate as a 3D model. For example, some of the empirical models utilized in the 1D model have been found to under predict the stenosis pressure drop when compared to 3D CFD. Thus, there is a need for approaches that can attain comparable accuracy to that obtained within 3D CFD while maintaining drastically lower computation times.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a computer-implemented method is provided. The method includes generating, via a processor, synthetic vessels. The method also includes performing, via the processor, three-dimensional (3D) computational fluid dynamics (CFD) on the synthetic vessels for different flow rates to generate 3D CFD data. The method further includes extracting, via the processor, 3D image patches from the synthetic vessels. The method even further includes obtaining, via the processor, pressure drops across the 3D image patches from the 3D CFD data. The method yet further includes training, via the processor, a deep neural network utilizing the 3D image patches, the pressure drops, and associated flow rates to generate a trained deep neural network.

In another embodiment, one or more non-transitory computer-readable media are provided. The computer-readable media encode one or more processor-executable routines. The one or more routines, when executed by a processor, cause acts to be performed. The acts include generating synthetic vessels. The acts also include performing three-dimensional (3D) CFD on the synthetic vessels for different flow rates to generate 3D CFD data. The acts further include extracting 3D image patches from the synthetic vessels. The acts even further include obtaining pressure drops across the 3D image patches from the 3D CFD data. The acts yet further include training a deep neural network utilizing the 3D image patches, the pressure drops, and associated flow rates to generate a trained deep neural network.

In a further embodiment, a processor-based system is provided. The processor-based system includes a memory encoding one or more processor-executable routines. The routines, when executed cause acts to be performed. The acts include generating synthetic vessels. The acts also include performing 3D CFD on the synthetic vessels for different flow rates to generate 3D CFD data. The acts further include extracting 3D image patches from the synthetic vessels. The acts even further include obtaining pressure drops across the 3D image patches from the 3D CFD data. The acts yet further include training a deep neural network utilizing the 3D image patches, the pressure drops, and associated flow rates to generate a trained deep neural network. The processor-based system also includes a processor configured to access and execute the one or more routines encoded by the memory.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
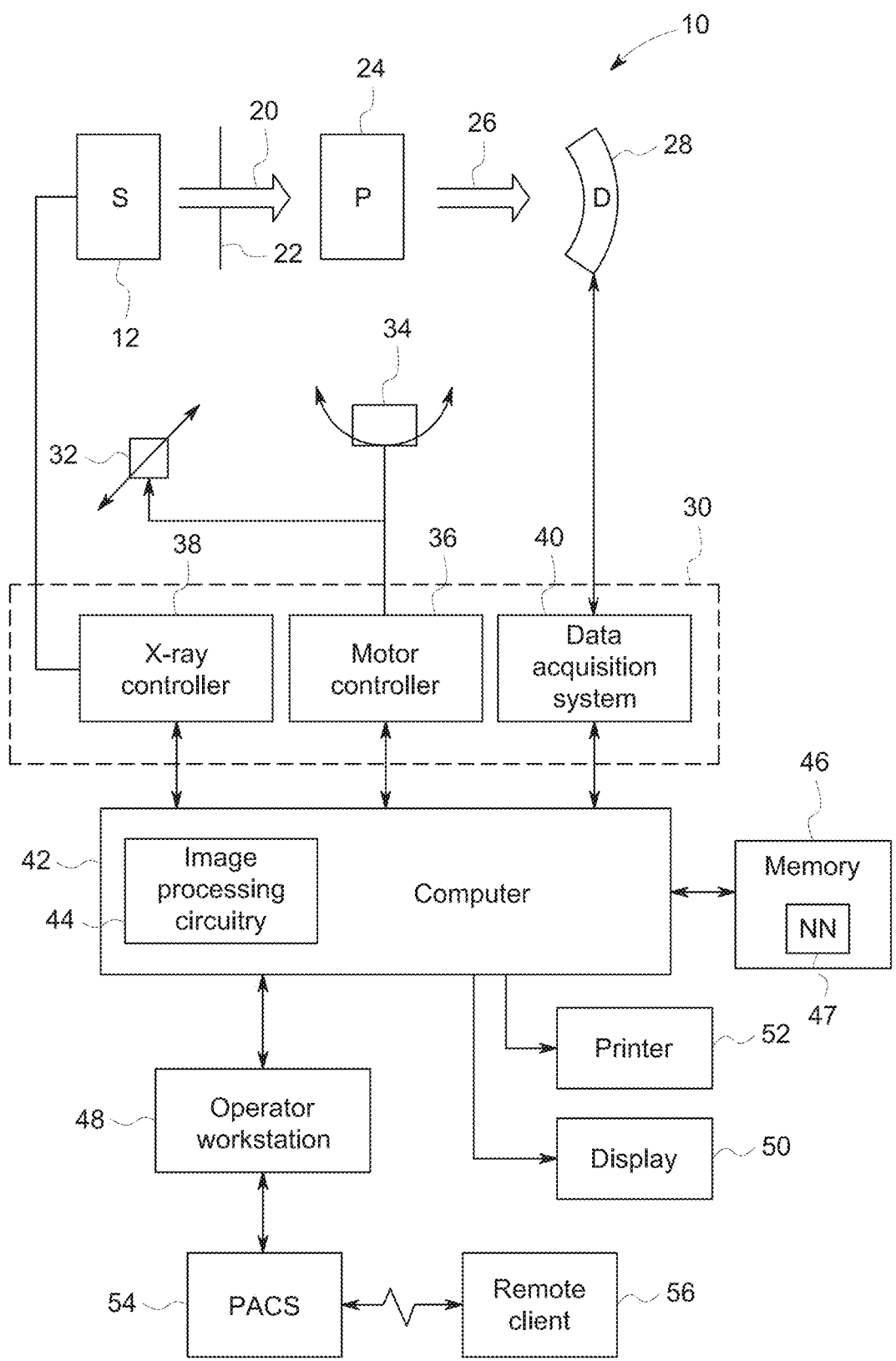
FIG. 1 is a schematic illustration of an embodiment of a computed tomography (CT) system configured to acquire CT images of a patient and process the images, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Some generalized information is provided to provide both general context for aspects of the present disclosure and to facilitate understanding and explanation of certain of the technical concepts described herein.

Deep-learning (DL) approaches discussed herein may be based on artificial neural networks, and may therefore encompass one or more of deep neural networks, fully connected networks, convolutional neural networks (CNNs), perceptrons, encoders-decoders, recurrent networks, wavelet filter banks, u-nets, generative adversarial networks (GANs), or other neural network architectures. The neural networks may include shortcuts, activations, batch-normalization layers, and/or other features. These techniques are referred to herein as deep-learning techniques, though this terminology may also be used specifically in reference to the use of deep neural networks, which is a neural network having a plurality of layers.

As discussed herein, deep-learning techniques (which may also be known as deep machine learning, hierarchical learning, or deep structured learning) are a branch of machine learning techniques that employ mathematical representations of data and artificial neural networks for learning and processing such representations. By way of example, deep-learning approaches may be characterized by their use of one or more algorithms to extract or model high-level abstractions of a type of data-of-interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data. In general, the processing from one representation space to the next-level representation space can be considered as one 'stage' of the process. Each stage of the process can be performed by separate neural networks or by different parts of one larger neural network.

The present disclosure provides systems and methods for predicting coronary artery pressure drop. The disclosed embodiments utilize deep neural networks to learn 3D CFD model predictions. In particular, a deep neural network is trained utilizing image patches (e.g., 3D image patches) extracted from synthetically generated vessels and the pressure drops occurring across these image patches (e.g., obtained from 3D CFD). The trained deep neural network is then used to predict the pressure drops across segmented image patches extracted from vessels in clinical image data (e.g., computed tomography angiography (CTA) data). The disclosed embodiments enable estimation of FFR with comparable accuracy to 3D CFD but with drastically lower computation times. Although described in the context of coronary artery disease, the methods provided are suitable for assessing the severity of vasculature narrowing anywhere in human anatomy, which may be due to atherosclerosis, other disease processes, general vasculature malformations, or the like.

With the foregoing discussion in mind, FIG. 1 illustrates an embodiment of an imaging system 10 for acquiring and processing image data in accordance with aspects of the present disclosure. Although the following embodiments are discussed in terms of the computed tomography (CT) imaging system, the embodiments may also be utilized with other imaging systems (e.g., X-ray, PET, CT/PET, SPECT, nuclear CT, magnetic resonance imaging, etc.). In the illustrated embodiment, system 10 is a CT system designed to acquire X-ray projection data, to reconstruct the projection data into one or more tomographic images, and to process the image data for display and analysis. The CT imaging system 10 includes an X-ray source 12. As discussed in detail herein, the source 12 may include one or more X-ray sources, such as an X-ray tube or solid-state emission structures. The X-ray source 12, in accordance with present embodiments, is configured to emit an X-ray beam 20 at one or more energies.

In certain implementations, the source 12 may be positioned proximate to a collimator 22 used to define the size and shape of the one or more X-ray beams 20 that pass into a region in which a subject 24 (e.g., a patient) or object of interest is positioned. The subject 24 attenuates at least a portion of the X-rays. Resulting attenuated X-rays 26 impact a detector array 28 formed by a plurality of detector elements. Each detector element produces an electrical signal that represents the intensity of the X-ray beam incident at the position of the detector element when the beam strikes the detector 28. Electrical signals are acquired and processed to generate one or more scan datasets or reconstructed images.

A system controller 30 commands operation of the imaging system 10 to execute examination and/or calibration protocols and to process the acquired data. With respect to the X-ray source 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12, and to process the data acquired by the detector 28 in accordance with the steps and processes discussed herein. In one embodiment, the system controller 30 may be implemented as all or part of a processor-based system such as a general-purpose or application-specific computer system.

The source 12 may be controlled by an X-ray controller 38 contained within the system controller 30. The X-ray controller 38 may be configured to provide power and timing signals to the source 12. The system controller 30 may include a data acquisition system (DAS) 40. The DAS 40 receives data collected by readout electronics of the detector 28, such as sampled analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40. The computer 42 may include processing circuitry 44 (e.g., image processing circuitry). The computer 42 may include or communicate with one or more non-transitory memory devices 46 that can store data processed by the computer 42, data to be processed by the computer 42, or instructions to be executed by a processor (e.g., processing circuitry 44) of the computer 42. For example, the processing circuitry 44 of the computer 42 may execute one or more sets of instructions stored on the memory 46, which may be a memory of the computer 42, a memory of the processor, firmware, or a similar instantiation. In accordance with present embodiments, the memory 46 stores sets of instructions that, when executed by the processor, perform image processing methods as discussed herein. The memory 46 also stores one or more algorithms and/or neural networks 47 that may be utilized in estimating or predicting coronary artery pressure drop across segmented mage patches extracted from clinical data (e.g., imaging data) as described in greater detail below.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, to observe reconstructed images, to control imaging, and so forth. Additionally, the system 10 may include a printer 52 coupled to the operator workstation 48 and configured to print images. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote client 56, radiology department information system (RIS), hospital information system (HIS) or to an internal or external network, so that others at different locations can gain access to the image data.

Further, the computer 42 and operator workstation 48 may be coupled to other output devices, which may include standard or special-purpose computer monitors and associated processing circuitry. One or more operator workstations 48 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

While the preceding discussion has treated the various exemplary components of the imaging system 10 separately, these various components may be provided within a common platform or in interconnected platforms. For example, the computer 42, memory 46, and operator workstation 48 may be provided collectively as a general- or special-purpose computer or workstation configured to operate in accordance with the aspects of the present disclosure. In such embodiments, the general- or special-purpose computer may be provided as a separate component with respect to the data acquisition components of the system 10 or may be provided in a common platform with such components. Likewise, the system controller 30 may be provided as part of such a computer or workstation or as part of a separate system dedicated to image acquisition.

Figure 2:
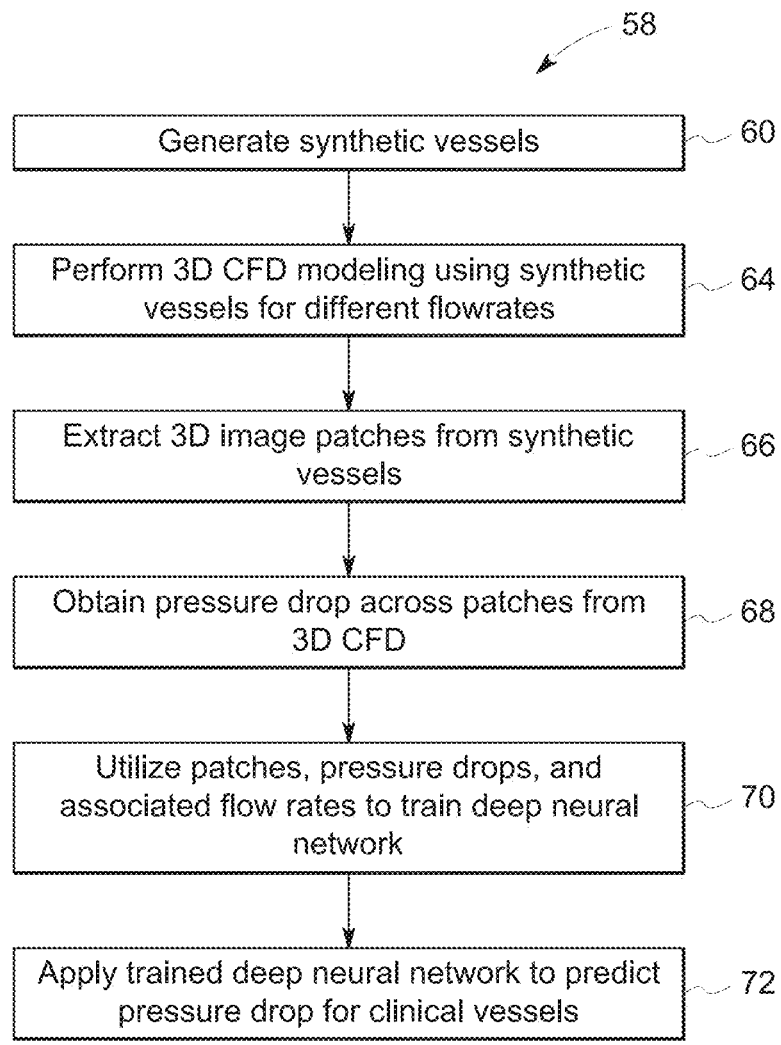
FIG. 2 is a flow chart of a method for training and utilizing a neural network for predicting a pressure drop (e.g., coronary artery pressure drop), in accordance with aspects of the present disclosure.
Figure 3:
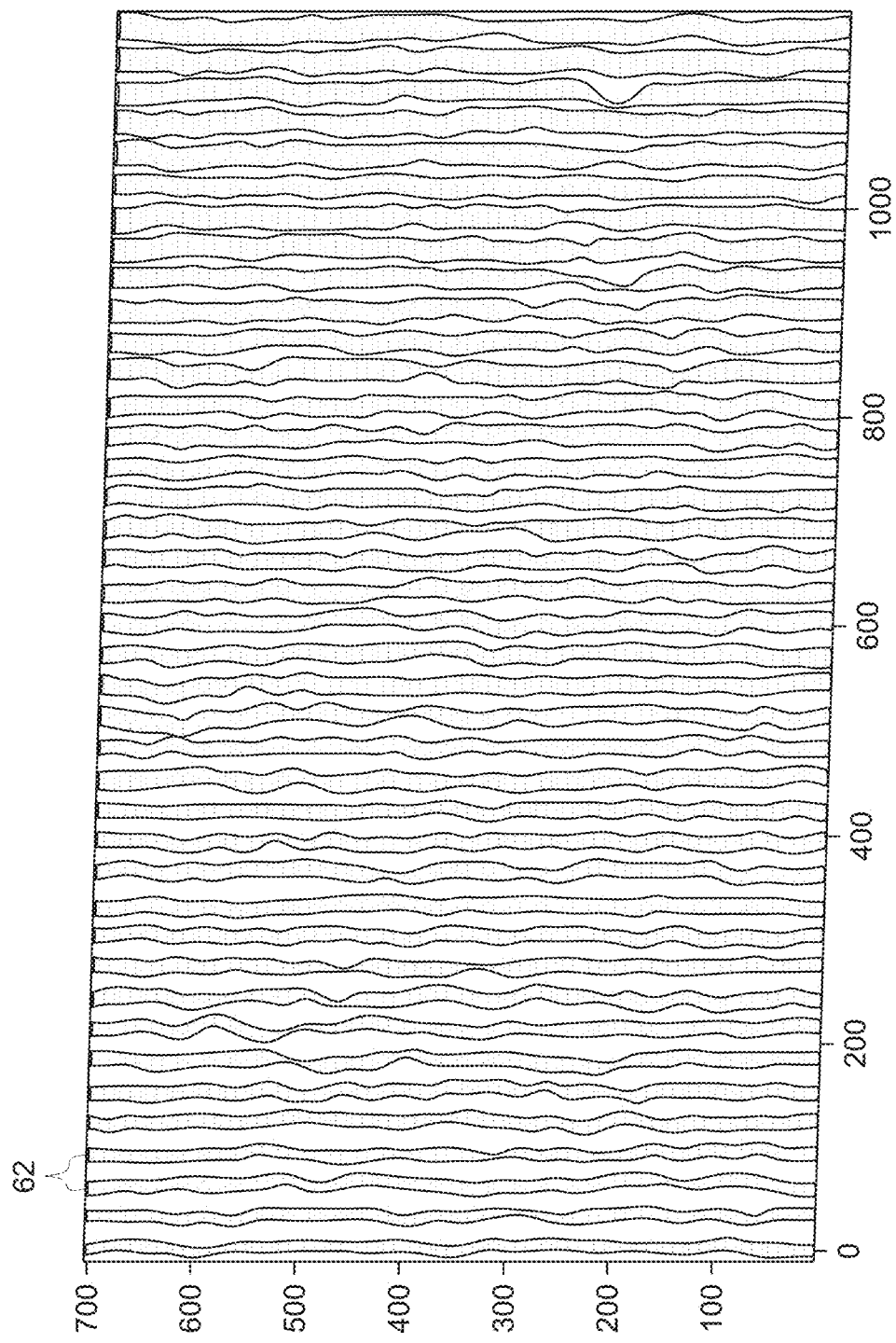
FIG. 3 is graphical representation of example of generated synthetic vessels, in accordance with aspects of the present disclosure.

FIG. 2 is a flow chart of a method 58 for training and utilizing a neural network for predicting a pressure drop (e.g., coronary artery pressure drop). Some or all of the steps of the method 58 may be performed by the computer 42, operator workstation 48, and/or a remote computing device. One or more steps of the illustrated method 58 may performed in a different order from the order depicted in FIG. 2 and/or simultaneously. The method 58 includes generating synthetic vessels (e.g., synthetic blood vessels) (block 60). In certain embodiments, a mathematical model (e.g., Lindenmayer system) may be utilized to generate the synthetic vessels. The process of synthetic vessel generation can be broken down into two steps: the vessel centerline generation and extraction of the vessel boundary for each slice. The vessel centerline generation involves the generation of a 3D random noise field, which is smoothed and thresholded with two kernels of different scales. The sum of these results is further smoothed and tapered in the axial direction. The center of mass is computed for each slice and then scaled and smoothed in the axial direction. Next, a series of stenosis locations are randomly positioned, and each is associated with a set of random parameters, including skew, depth, length, eccentricity, shape factor, and other parameters. Based on these parameters, the nominal centerline position and the nominal radius are smoothly modified in the areas of stenosis. The vessel boundary extraction involves evaluating the sum of a parabolic function and a modified noise field at each slice. The parabolic function is offset and scaled so that (in the absence of noise) it would take on a positive value at all points that are within the nominal radius of the nominal centerline position. Adding the noise field provides distortion to this boundary and can either increase or decrease the cross-sectional area moderately. The noise field intensity may be modulated by a factor of 2 in the axial direction, with higher noise near the middle of the vessel in order to provide a range of distortion levels. The slope of the parabola may be adjusted based on the nominal radius to ensure the sensitivity of the boundary to the noise field is not strongly dependent on the nominal radius. A surface mesh is generated from the boundaries extracted from each slice and the cross-sectional coordinates of the mesh are smoothed by convolving each point with its mesh neighborhood. The generated synthetic vessels lack branches. Examples of generated synthetic vessels 62 are shown in FIG. 3.

Returning to the method 58, the method 58 includes performing 3D CFD modeling using the generated synthetic vessels for different flow rates (e.g., volume flow rates) (block 64). The different flow rates are applied to each synthetic vessel. Blood is assumed to an incompressible, Newtonian fluid in the proposed process and the equations governing its motion are the incompressible Navier-Stokes equations. A commercial solver is used to solve these equations. At the inlet of each synthetic vessel, a randomly chosen flow rate between 0 and 400 milliliters/minute is imposed. The vessel walls are assumed to be rigid and no-slip and no-flow-through boundary conditions are imposed there. Zero pressure boundary conditions are imposed at the vessel exit. For each vessel, CFD calculations are performed for seven different randomly chosen flows (e.g., flow rates). The convergence of the CFD calculations is judged based on how much the residual at each iteration has dropped from their initial values and only the converged cases are post-processed to obtain the pressure drops.

The method 58 also includes extracting 3D image patches from the generated synthetic vessels to generate training data (block 66). In certain embodiments, 3D image patches are extracted at regular intervals from the synthetic vessels. In certain embodiments, the 3D patches are overlapping. In certain embodiments, the 3D image patches may be extracted randomly. The axial patch dimension (e.g., axial distance) is chosen to be much smaller than the vessel length while the dimensions in the other two directions are chosen large enough to encompass the largest synthetic vessel cross section. In certain embodiments, the axial patch dimension is the same for each 3D image patch.

The method 58 further includes obtaining pressure drops across the 3D image patches from the 3D CFD data obtained above (block 68). For each of these 3D image patches, a total pressure drop across an entire axial length of the patch or a portion of the axial patch length is determined from the 3D CFD calculation. By extracting the pressure drop over only a portion of the axial patch length as opposed to the whole length, the influence of upstream and downstream patch geometric features on the pressure drop can be incorporated into a deep neural network. Instead of extracting a single total pressure drop over the entire axial patch length, in certain embodiments, multiple pressure drops over portions of the axial patch length are extracted.

The method 58 still further includes utilizing the 3D image patches and associated pressure drops and flow rates to train a deep neural network (block 70). The structure of the deep neural network is described in greater detail below. For each of the 3D image patches, a binary mask is generated using a CT simulation tool. The binary mask and volume flow (e.g., volume flow rate) through the vessel are provided as inputs to the deep-learning network. The output from the deep neural network is the pressure drop across the whole axial length or a portion of the axial length of the 3D image patch with the corresponding label data being the 3D CFD determined value. In certain other embodiments, the output from the deep neural network is multiple pressure drops over portions of the axial patch length. Since a large portion of the synthetic vessel is healthy and a stenosis only occurs occasionally, most of the 3D image patches extracted by the above approach will be in the healthy section. As a result, a considerable number of the patch pressure drops will be small. Indeed, if one were to plot a histogram of the training data pressure drops, a highly imbalanced distribution may be seen with a large fraction of the 3D image patches having pressure drops between approximately 0 to 1 mm Hg and very few patches with pressure drops between approximately 49 to 50 mm Hg corresponding to high degrees of vessel stenosis. Due to this imbalance the training loss will be skewed towards patches with pressure drops in the range of approximately 0 to 1 mm Hg. To avoid this issue, augmentation of patches outside the 0 to 1 mm Hg range may be performed. The augmentations may be done by rotating the 3D image patch as well as by in-plane translations. These transformations do not affect the patch pressure drop. Further, an unlimited number of synthetic vessels could be generated, while increasing the percentage of highly stenosed vessels in the training data for the deep neural network.

The method 58 yet further includes applying the trained deep neural network to vessels (e.g., blood vessels) in a clinical image (e.g., CTA image data) to predict a pressure drop (e.g. coronary artery pressure drop) for least a portion of at least one vessel in the clinical image (block 72). The utilization of the trained deep neural network is described in greater detail below.

Figure 4:
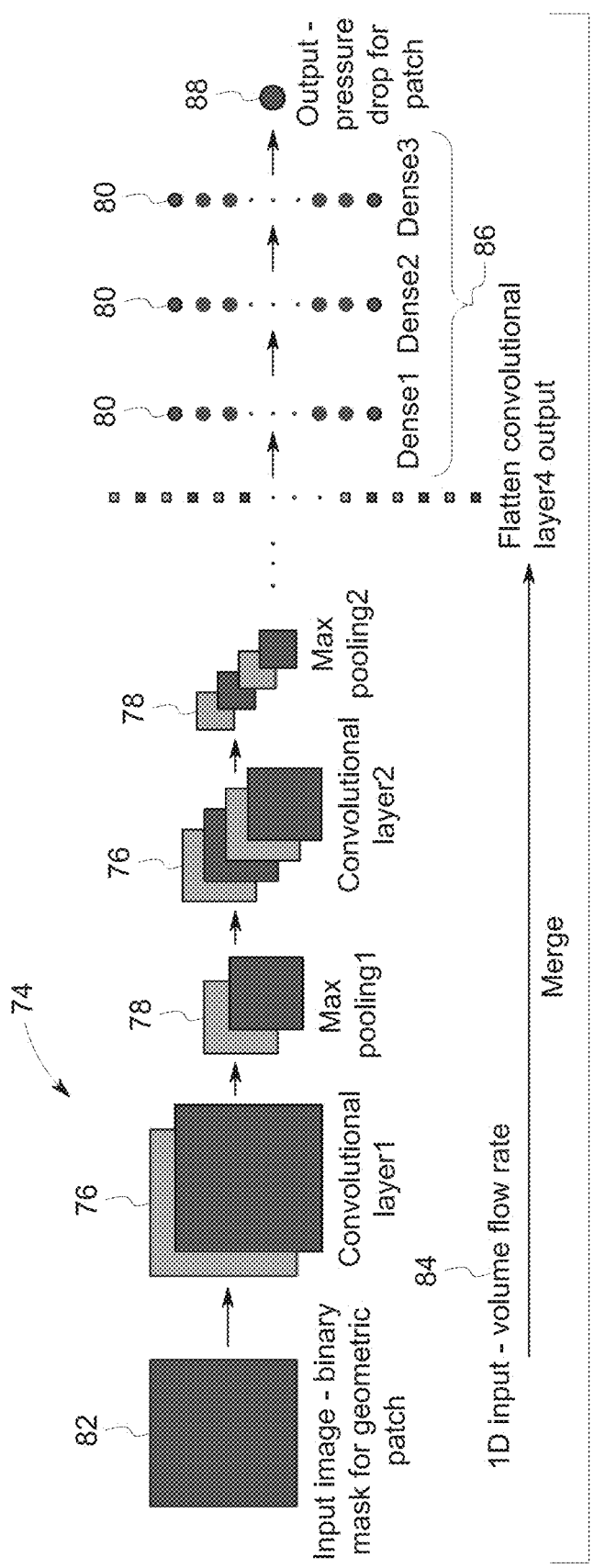
FIG. 4 illustrates an example of a convolutional neural network architecture for predicting a pressure drop, in accordance with aspects of the present disclosure.

Different types of network architecture may be utilized for the deep neural network described herein. FIG. 4 illustrates an example of a convolutional neural network (CNN) architecture 74 for predicting a pressure drop. The CNN 74 may include convolutional layers 76 alternating with max pooling layers 78 followed by dense layers 80 with neurons used. When training the network, a binary mask image 82 corresponding to a 3D geometric patch extracted from a synthetic vessel is provided as input to the convolutional layers 76. After feature extraction, the features are merged with the input flow rate 84 and provided as input to the dense network 86. An output 88 from the dense network 86 is the predicted pressure drop from the patch with the CFD obtained pressure drop as the label data. In certain embodiments, the output 88 from the dense network 86 will be more than one number corresponding to multiple pressure drops predicted over portions of the axial patch length. The loss function minimized during training in the CNN architecture 74 is the mean square error between the predicted pressure drop and the CFD obtained pressure drop.

In certain embodiments, other loss function formulations may be utilized. One such example is a physics informed neural network (PINN) where the loss function is the residual in the equations governing the physics of the problem. For the particular problem disclosed here within the governing equations are the incompressible Navier-Stokes equations and the loss function would include the residuals in the mass and momentum conservation equations when using PINNs. The loss function would also include residuals in the imposed boundary conditions. In addition, the loss function may also include the error between the predicted pressure drop and the CFD obtained pressure drop. The network architecture for the PINN would be similar to the one depicted in FIG. 4. Similarly, the inputs to the network would be the binary mask and the flow rate. In addition, randomly chosen co-ordinate positions within the interior and boundaries of the 3D geometric patch would also be provided as inputs to the network. The output from the network would be the velocities and pressures at the randomly chosen co-ordinate positions. From the predicted pressures, the pressure drop within the patch may be determined. The predicted flow may also be used to determine quantities such as wall shear stress within the patch.

Figure 5:
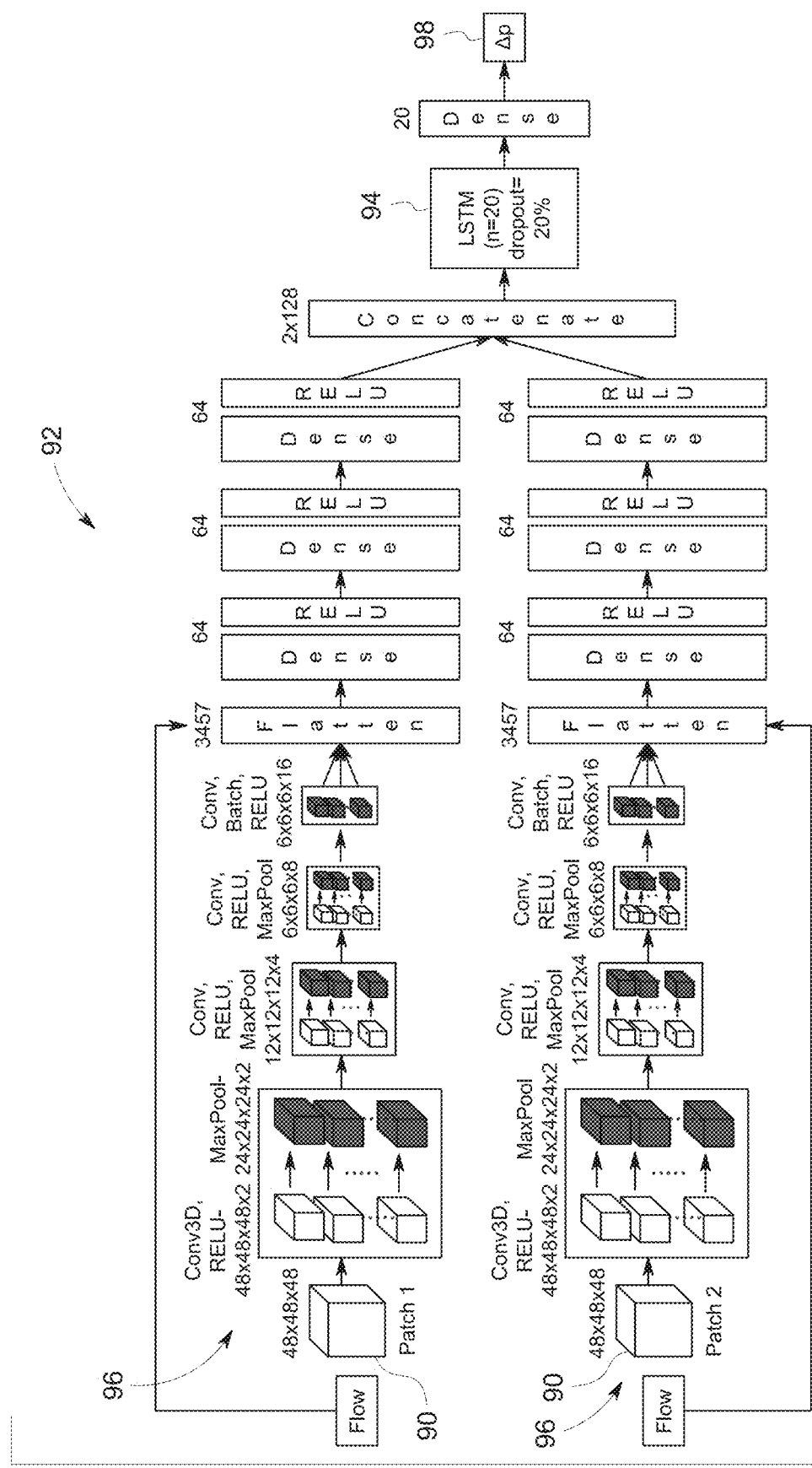
FIG. 5 illustrates an example of a multipath neural network having a long short-term memory (LSTM) cell for predicting a predicting a pressure drop, in accordance with aspects of the present disclosure.

An alternative network architecture would be using two or more patches 90 in a multipath network 92 along with an LSTM cell 94 as depicted in FIG. 5. The hypothesis here is, given the 3D geometry and flow in two or more consecutive patches 90 (considered as time points in the LSTM cell 94), the pressure drop can be computed for the downstream patch 90. The network architecture is similar to FIG. 4 except two or more separate paths 96 would exist for the convolution chain of each patch 90. Finally, the convolution output for each patch 90 will be concatenated as timepoints for input to the LSTM cell 94 with pressure drop as output 98 of the network 92. This is a case where the LSTM cell 94 is used for regression analysis, where given some observed variables (e.g., 3D geometry and flow) for certain time steps (number of patches 90), the target variable (pressure drop) value is predicted.

Figure 6:
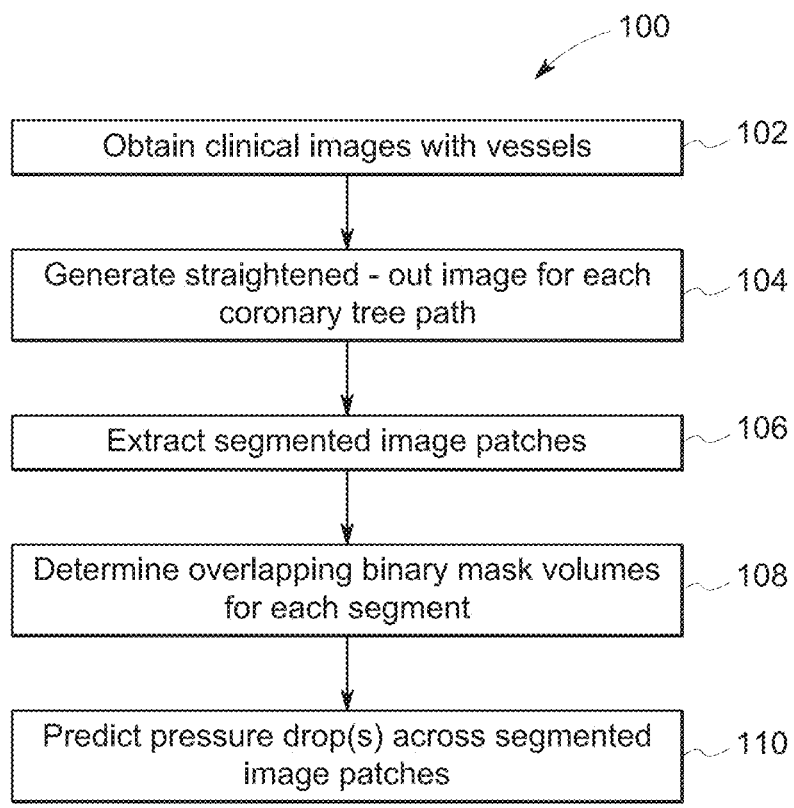
FIG. 6 is a flow chart of a method for utilizing a trained neural network for predicting a pressure drop (e.g., coronary artery pressure drop), in accordance with aspects of the present disclosure.

FIG. 6 is a flow chart of a method 100 for utilizing a trained neural network for predicting a pressure drop (e.g., coronary artery pressure drop). Some or all of the steps of the method 100 may be performed by computer 42, operator workstation 48, and/or a remote computing device. One or more steps of the illustrated method 100 may performed in a different order from the order depicted in FIG. 6 and/or simultaneously. The training of the deep neural network described above is done entirely using synthetic vessels without any branches. However, in reality, there are branches in clinical vessels. To apply the trained network to these vessels, the following method 100 is utilized. The method 100 includes obtaining or receiving clinical images (e.g., 3D CTA images) with vessels (block 102). The method 100 also includes generating straightened-out images for each coronary tree path within respective clinical images (block 104). Vessel centerlines are determined along the coronary tree. Then, for each coronary tree path (a path here is defined as starting from the left or right coronary ostia and ending at a terminal point in the tree), the image normal to the vessel centerline is determined. This helps to transform each coronary tree path and the surrounding image from physical space to a straightened-out space.

The method 100 further includes extracting segmented 3D image patches (block 106). A deep-learning algorithm, a traditional segmentation algorithm (e.g., level-set segmentation), active contour model, atlas, or a combination thereof is utilized to segment the vessels that include each straightened-out coronary path. The method 100 even further includes, for each vessel segment within a straightened-out coronary path, determining overlapping binary mask volumes that make up each segment (block 108).

The method 100 still further includes predicting (or estimating) one or more pressure drops across each segmented binary mask volume (block 110). For each binary mask volume, the trained deep neural network (as described above) is run for multiple flow rates and a pressure drop ($\Delta p$) versus flow rate (Q) curve of the form $\Delta p = AQ + BQ^2$ is constructed. Constructing such a curve avoids having to call the deep neural network multiple times during hyperemia flow optimization and helps reduce overall run time. Since a given vessel segment may belong to multiple coronary paths, the A and B coefficients are averaged over the respective paths. The averaged coefficients are then used to determine the pressure drop through the coronary tree under both rest and hyperemia.

Figure 7:
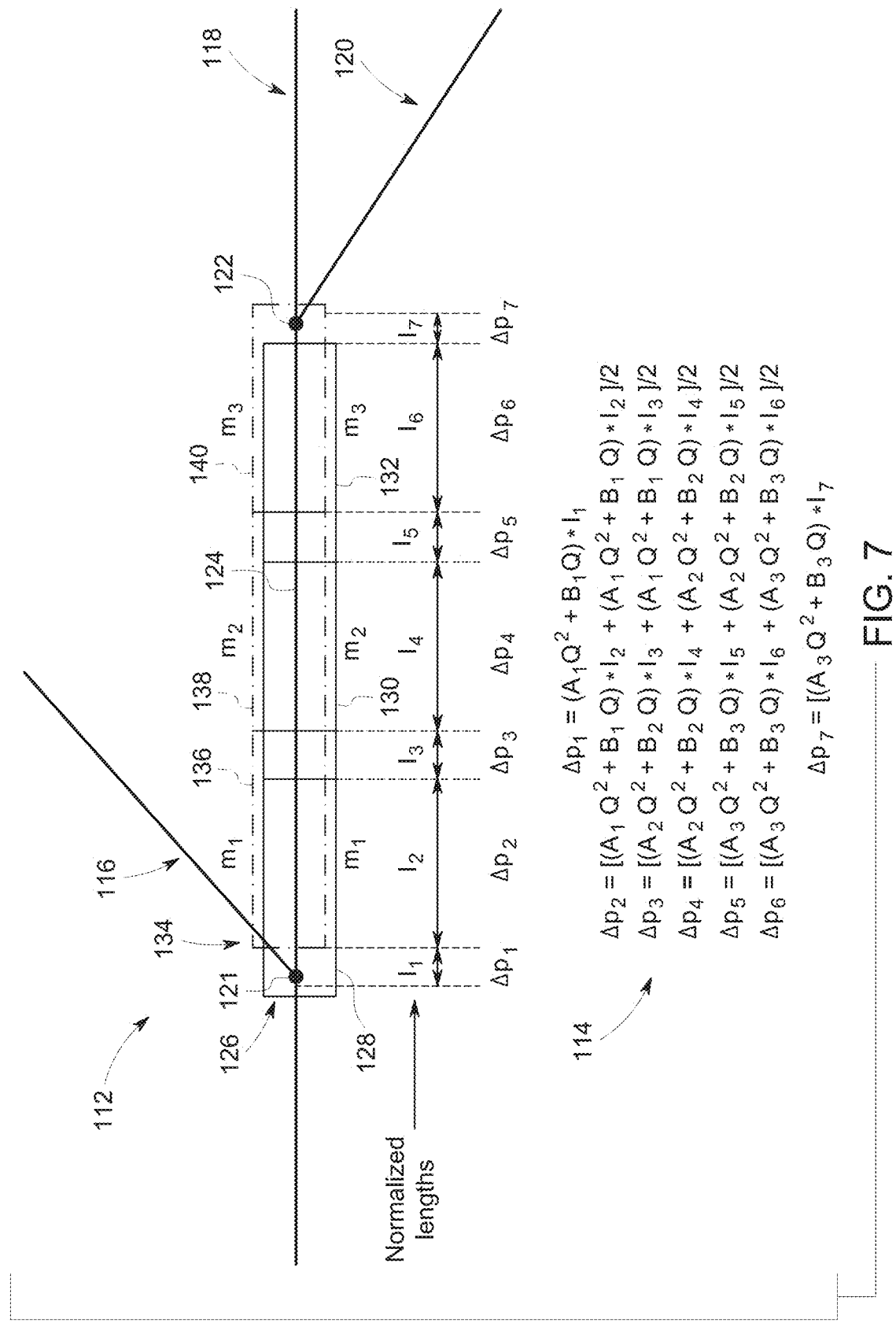
FIG. 7 is a schematic representation of a segmented vessel within a coronary tree with overlapping binary mask volumes and associated equations for determining pressure drop, in accordance with aspects for the present disclosure.

FIG. 7 illustrates a schematic representation of a segmented vessel within a coronary tree 112 and associated equations 114 for determining pressure drop as discussed in the method 100. The depicted segmented coronary tree 112 in FIG. 7 includes multiple straightened-out coronary paths 116, 118, 120. The coronary tree 112 also includes two branch points 121, 122 between the different coronary paths 116, 118, 120. Branch point 121 is common to the coronary paths 116, 118. Branch point 122 is common to the coronary paths 118, 120.

For a vessel segment 124 (belonging to coronary paths 118, 120) extending between the branch points 121, 122, a first region 126 includes binary mask volumes (represented by boxes 128, 130, 132 with labels $m_1$, $m_2$, and $m_3$, respectively) and a second region 134 includes binary mask volumes (represented by boxes 136, 138, 140 with labels $m_1$, $m_2$, and $m_3$, respectively). Binary mask volumes in region 126 overlap with binary mask volumes in region 134. For example, binary mask volume 128 overlaps with binary mask volume 136, binary mask volume 130 overlaps with binary mask volumes 136 and 138, binary mask volume 132 overlaps with binary mask volumes 138 and 140.

Normalized length $l_1$ represents the non-overlapping length between binary mask volume 128 and binary mask volume 136 (i.e., how far binary mask volume 128 extends beyond binary mask volume 136). Normalized length $l_2$ represents the overlapping length between binary mask volume 128 and binary mask volume 136. Normalized length $l_3$ represents the overlapping length between binary mask volume 130 and binary mask volume 136. Normalized length $l_4$ represents the overlapping length between binary mask volume 130 and binary mask volume 138. Normalized length $l_5$ represents the overlapping length between binary mask volume 132 and binary mask volume 138. Normalized length $l_6$ represents the overlapping length between binary mask volume 132 and binary mask volume 140. Normalized length $l_7$ represents the non-overlapping length between mask volume 140 and binary mask volume 132 (i.e., how far binary mask volume 140 extends beyond binary mask volume 132). Pressure drops $\Delta p_1$, $\Delta p_2$, $\Delta p_3$, $\Delta p_4$, $\Delta p_5$, $\Delta p_6$, and $\Delta p_7$ occur across normalized lengths $l_1$, $l_2$, $l_3$, $l_4$, $l_5$, $l_6$, and $l_7$, respectively.

The equations 114 are for calculating the pressure drops $\Delta p_1$, $\Delta p_2$, $\Delta p_3$, $\Delta p_4$, $\Delta p_5$, $\Delta p_6$, and $\Delta p_7$ across normalized lengths (axial lengths) $l_1$, $l_2$, $l_3$, $l_4$, $l_5$, $l_6$, and $l_7$, respectively. In the equation 114 for $\Delta p_1$, the coefficients $A_1$ and $B_1$ are derived from the binary mask volume 128 by running the trained deep neural network for multiple flow rates. In the equation 114 for $\Delta p_2$, the coefficients $A_1$ and $B_1$ on the left side are derived from the binary mask volume 128 and the coefficients $A_1$ and $B_1$ on the right side are derived from the binary mask volume 136. In the equation 114 for $\Delta p_3$, the coefficients $A_2$ and $B_2$ on the left side are derived from the binary mask volume 130 and the coefficients $A_1$ and $B_1$ on the right side are derived from the binary mask volume 136. In the equation 114 for $\Delta p_4$, the coefficients $A_2$ and $B_2$ on the left side are derived from the binary mask volume 130 and the coefficients $A_2$ and $B_2$ on the right side are derived from the binary mask volume 138. In the equation 114 for $\Delta p_5$, the coefficients $A_3$ and $B_3$ on the left side are derived from the binary mask volume 132 and the coefficients $A_2$ and $B_2$ on the right side are derived from the binary mask volume 138. In the equation 114 for $\Delta p_6$, the coefficients $A_3$ and $B_3$ on the left side are derived from the binary mask volume 132 and the coefficients $A_3$ and $B_3$ on the right side are derived from the binary mask volume 140. In the equation 114 for $\Delta p_7$, the coefficients $A_3$ and $B_3$ are derived from the binary mask volume 140.

Technical effects of the disclosed subject matter include providing systems and methods for predicting coronary artery pressure drop. The disclosed embodiments utilize deep neural networks to learn 3D CFD model predictions. In particular, a deep neural network is trained utilizing image patches (e.g., 3D image patches) extracted from synthetically generated vessels and the pressure drops across these image patches (e.g., obtained from 3D CFD). The trained deep neural network is then used to predict the pressure drops across segmented image patches extracted from vessels in clinical image data (e.g., computed tomography angiography (CTA) data). The disclosed embodiments enable estimation of FFR with comparable accuracy to 3D CFD but with drastically lower computation times.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method, comprising:
   generating, via a processor, synthetic vessels;
   performing, via the processor, three-dimensional (3D) computational fluid dynamics (CFD) on the synthetic vessels for different flow rates to generate 3D CFD data;
   extracting, via the processor, 3D image patches from the synthetic vessels;
   obtaining, via the processor, pressure drops across the 3D image patches from the 3D CFD data; and
   training, via the processor, a deep neural network utilizing the 3D image patches, the pressure drops, and associated flow rates to generate a trained deep neural network.

2. The computer-implemented method of claim 1, further comprising applying, via the processor, the trained deep neural network to a vessel in clinical image data to predict a pressure drop for at least a portion of the vessel.

3. The computer-implemented method of claim 2, wherein applying the trained deep neural network comprises applying the trained deep neural network to at least one segmented image patch of the vessel to predict one or more pressure drops across the at least one segmented image patch.

4. The computer-implemented method of claim 3, further comprising:
   obtaining, via the processor, clinical images;
   generating, via the processor, straightened-out images for each coronary tree path in the clinical images;
   generating, via the processor, a segmented image from each straightened-out image of the straightened-out images to generate a plurality of segmented images;
   determining, via the processor, overlapping binary mask volumes for each vessel segment within each coronary tree path from the plurality of segmented images; and
   applying, via the processor, the trained deep neural network to each overlapping binary mask volume of the overlapping binary mask volumes to predict the pressure drops within each vessel segment.

5. The computer-implemented method of claim 4, further comprising, for each overlapping binary mask volume of the overlapping binary mask volumes, running, via the processor, the trained deep neural network for two or more flow rates to construct a pressure drop ($\Delta p$) versus a flow rate (Q) curve of a form $\Delta p = AQ + BQ^2$, wherein coefficients A and B averaged over the overlapping binary mask volumes are used to determine the pressure drop through a respective coronary tree path under both rest and hyperemia.

6. The computer-implemented method of claim 1, wherein the 3D image patches overlap with each other.

7. The computer-implemented method of claim 1, further comprising generating, via the processor, a respective binary mask for each 3D image patch of the 3D image patches.

8. The computer-implemented method of claim 7, further comprising inputting, via the processor, the respective binary mask for each 3D image patch of the 3D image patches into the trained deep neural network along with respective pressure drops and respective flow rates.

9. One or more non-transitory computer-readable media encoding one or more processor-executable routines, wherein the one or more processor-executable routines, when executed by a processor, cause acts to be performed comprising:
   generating synthetic vessels;
   performing three-dimensional (3D) computational fluid dynamics (CFD) on the synthetic vessels for different flow rates to generate 3D CFD data;
   extracting 3D image patches from the synthetic vessels;
   obtaining pressure drops across the 3D image patches from the 3D CFD data; and
   training a deep neural network utilizing the 3D image patches, the pressure drops, and associated flow rates to generate a trained deep neural network.

10. The one or more non-transitory computer-readable media of claim 9, wherein the one or more processor-executable routines, when executed by the processor, cause further acts to be performed comprising applying the trained deep neural network to a vessel in clinical image data to predict a pressure drop for at least a portion of the vessel.

11. The one or more non-transitory computer-readable media of claim 10, wherein applying the trained deep neural network comprises applying the trained deep neural network to at least one segmented image patch of the vessel to predict the pressure drop across the at least one segmented image patch.

12. The one or more non-transitory computer-readable media of claim 11, wherein the one or more processor-executable routines, when executed by the processor, cause further acts to be performed comprising:
   obtaining clinical images;
   generating straightened-out images for each coronary tree path in the clinical images;
   generating a segmented image from each straightened-out image of the straightened-out images to generate a plurality of segmented images;
   determining overlapping binary mask volumes for each vessel segment within each coronary tree path from the plurality of segmented images; and
   applying the trained deep neural network to each overlapping binary mask volume of the overlapping binary mask volumes to predict the pressure drops within each vessel segment.

13. The one or more non-transitory computer-readable media of claim 9, wherein the 3D image patches overlap with each other.

14. The one or more non-transitory computer-readable media of claim 9, wherein the one or more processor-executable routines, when executed by the processor, cause further acts to be performed comprising generating a respective binary mask for each 3D image patch of the 3D image patches.

15. The one or more non-transitory computer-readable media of claim 14, wherein the one or more processor-executable routines, when executed by the processor, cause further acts to be performed comprising inputting the respective binary mask for each 3D image patch of the 3D image patches into the trained deep neural network along with respective pressure drops and respective flow rates.

16. A processor-based system, comprising:
   a memory encoding one or more processor-executable routines, wherein the one or more processor-executable routines, when executed cause acts to be performed comprising:
      generating synthetic vessels;
      performing three-dimensional (3D) computational fluid dynamics (CFD) on the synthetic vessels for different flow rates to generate 3D CFD data;
      extracting 3D image patches from the synthetic vessels;
      obtaining pressure drops across the 3D image patches from the 3D CFD data; and
      training a deep neural network utilizing the 3D image patches, the pressure drops, and associated flow rates to generate a trained deep neural network; and
   a processor configured to access and execute the one or more processor-executable routines encoded by the memory.

17. The processor-based system of claim 16, wherein the one or more processor-executable routines, when executed cause further acts to be performed comprising applying the trained deep neural network to a vessel in clinical image data to predict a pressure drop for at least a portion of the vessel.

18. The processor-based system of claim 17, wherein applying the trained deep neural network comprises applying the trained deep neural network to at least one segmented image patch of the vessel to predict the pressure drop across the at least one segmented image patch.

19. The processor-based system of claim 18, wherein the one or more processor-executable routines, when executed cause further acts to be performed comprising:
   obtaining clinical images;
   generating straightened-out images for each coronary tree path in the clinical images;
   generating a segmented image from each straightened-out image of the straightened-out images to generate a plurality of segmented images;
   determining overlapping binary mask volumes for each vessel segment within each coronary tree path from the plurality of segmented images; and
   applying the trained deep neural network to each overlapping binary mask volume of the overlapping binary mask volumes to predict the pressure drops within each vessel segment.

20. The processor-based system of claim 16, wherein the one or more processor-executable routines, when executed by the processor, cause further acts to be performed comprising:
   generating a respective binary mask for each 3D image patch of the 3D image patches; and
   inputting the respective binary mask for each 3D image patch of the 3D image patches into the trained deep neural network along with respective pressure drops and respective flow rates.

* * * * *